US00PP16625P3

(12) United States Plant Patent

Hasegawa

(10) Patent No.: US PP16,625 P3

(45) Date of Patent: Jun. 13, 2006

(54) CARNATION PLANT CALLED 'CFPC TESS'

(50) Latin Name: *Dianthus caryophyllus*
Varietal Denomination: CFPC Tess

(76) Inventor: Oscar T. Hasegawa, 1721 Burlington Dr., Salinas, CA (US) 93906

( * ) Notice: Subject to any disclaimer, the term of this patent is extended or adjusted under 35 U.S.C. 154(b) by 105 days.

(21) Appl. No.: 10/837,300

(22) Filed: Apr. 30, 2004

(65) Prior Publication Data

US 2005/0246808 P1 Nov. 3, 2005

(51) Int. Cl.
*A01H 5/00* (2006.01)

(52) U.S. Cl. ..... Plt./273

(58) Field of Classification Search ..... Plt./273, Plt./276, 277

See application file for complete search history.

*Primary Examiner*—Anne Marie Grunberg

(74) *Attorney, Agent, or Firm*—Christie, Parker & Hale, LLP

(57) ABSTRACT

A new and distinct variety of carnation plant characterized by large, full-size spray type flowers, which open fully without bursting the calyx and causing splits.

1 Drawing Sheet

Botanical classification: The present invention relates to a new and distinct variety of hybrid *Dianthus caryophyllus*. The varietal denominator of the new variety is 'CFPC Tess'.

BACKGROUND OF THE INVENTION

The present invention relates to a new and distinct variety of carnation plant, named 'CFPC Tess', which was originated by me from a cross made in a controlled breeding program. The female, or seed, parent is unpatented and identified as 990366; the male, or pollen, parent is an unknown seedling. The primary objective of the controlled breeding program was to produce a new purple-flowered cultivar for the 'Adorable' series of pot carnations. The closest commercial cultivar in color to the new cultivar of which I am aware is the carnation 'CFPC Passion' (U.S. Plant Pat. No. 10,416).

'CFPC Tess' differs from its female parent 990366, in having a purple flower color, while 990366 has a white flower color with markings. No comparison with male parent is possible, as the male parent is unknown. 'CFPC Tess' differs from its closest known commercial cultivar, 'CFPC Passion', in that 'CFPC Tess' is an 'Adorable' type carnation having a shorter stature, as well as a larger, fuller, more double flower.

SUMMARY OF THE INVENTION

Among the novel characteristics possessed by the new variety which distinguishes it is a large, full-spray type flower, which opens fully without bursting the calyx and causing splits. When grown in 4½ plastic pots in Salinas, Calif., plant diameter averages about 7 inches. Pinched plants are about 6½ inches tall and flowers are about 2 inches average diameter with a crown higher than about ⅞ inches. Foliage is about 3¼ inches long and about 5/16 inches wide.

Asexual reproduction and flowering of this new cultivar by side shoot cuttings as performed in Salinas, Calif., shows that the foregoing and other distinguishing characteristics come true to form and are established and transmitted through succeeding propagations.

BRIEF DESCRIPTION OF ILLUSTRATIONS

The accompanying photographic illustration shows a typical specimen of the new variety in color as nearly true as it is reasonably possible to make in a color illustration of this character.

DESCRIPTION OF THE NEW VARIETY

Referring now specifically to the new and distinct variety of carnation plant the following is a detailed description of 'CFPC Tess' with color description where indicated by reference to The Royal Horticultural Society Colour Chart, except where common terms of color definition are employed.

The new variety of carnation plant as herein described may vary in slight detail due to climatic, soil and cultural conditions under which the variety may be grown, the present description being of the variety as grown at Salinas, Calif.

Plant:

*Height*.—About 6½ inches tall.
*Form*.—Herbaceous.
*Growing habit*.—Semi-upright.
*Blooming habit*.—As a spray, pot variety.
*Blooming season*.—Year round.
*Rooting time*.—About 18 days.
*Number of new flower-bearing shoots per cutting*.—About 4 to 6 shoots per cutting.
*Mutation prone*.—No.
*Disease resistance*.—Superior to *Fusarium oxysporum, F. graminearum* and root-rots such as damping off, water molds and the like.
*Temperature tolerance*.—At least 60° F. to 90° F.

Foliage:

*Color*.—Upper side: near 136A; lower side: near 137B.

*Size*.—Length: about 3¼ inches; width: about 5/16 inches.

*Quantity*.—Numerous.

*Shape*.—Lanceloate.

*Texture*.—Smooth.

*Ribs*.—Central keel.

*Stem color*.—Near 138C.

Bud:

*Shape*.—Ovoid.

*Color*.—Near 138B.

*Size*.—Length: about 15/16 inches; diameter: about 7/16 inches.

Calyx:

*No. of lobes* (*sepals*).—Five.

*Size*.—Length: about 5/16 inches; width: about ¼ inches.

*Color*.—Outside: near 138B; inside: near 138C.

Bloom:

*Shape*.—Rounded.

*Size*.—Diameter (average): about 2 inches; depth (average): about ⅞ inches.

*Borne*.—As a spray.

*Color*.—General tonality: purple; Upper side: near 74A; Lower side: near 74B; Center: near 74A; Outer petals: near 74A.

*Permanence*.—Dry up on receptacle.

*Keeping quality*.—Very good, over three weeks.

*Fragrance*.—Slight.

Petalage:

*Number*.—Approximately Forty two.

*Outer petals*.—Length: about 1¾ inches; Width: about 1⅜ inches.

*Central petals*.—Length: about 1½ inches; Width: about ¾ inches.

*Texture*.—Smooth.

*Appearance*.—Shiny.

*Form*.—Fan-shaped.

Reproductive organs:

*Stamen*.—None (male sterile).

*Anthers*.—None.

*Filaments*.—None.

*Pistil*.—Number: one. Color: White (whiter than 155D).

*Stigma*.—Number: 3 (trilobed); Color: White (whiter than 155D) with tips of near 74B.

*Fertility*.—Male: sterile; Female: Not observed.

*Ovary*.—Shape: conical; Color: base near 138D, body near 138A, apex near 138A.

I claim:

1. A new and distinct variety of carnation plant identified as 'CFPC Tess', substantially as shown and described.

* * * * *

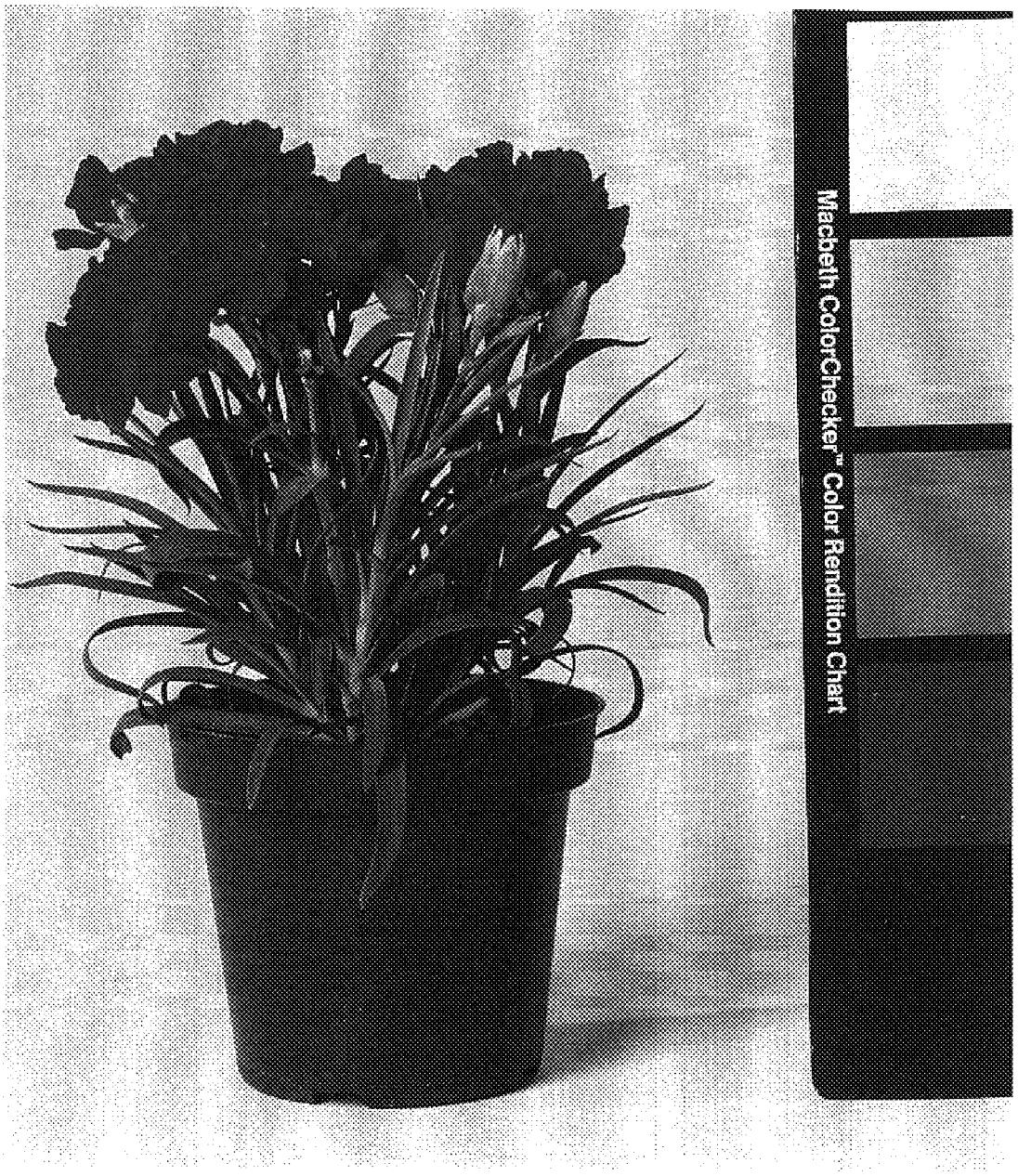
Macbeth ColorChecker™ Color Rendition Chart